(12) United States Patent
Elder et al.

(10) Patent No.: US 7,141,637 B2
(45) Date of Patent: Nov. 28, 2006

(54) METALLOCENE COMPOUNDS AND PROCESS FOR THE PREPARATION OF PROPYLENE POLYMERS

(75) Inventors: Michael J. Elder, Heidelbeg-Kirchheim (DE); Robert L. Jones, Jr., Heidelbeg-Kirchheim (DE)

(73) Assignee: Basell Polyolefine GmbH, Wesseling (DE)

( * ) Notice: Subject to any disclaimer, the term of this patent is extended or adjusted under 35 U.S.C. 154(b) by 45 days.

(21) Appl. No.: 10/496,253

(22) PCT Filed: Nov. 28, 2002

(86) PCT No.: PCT/EP02/13552
§ 371 (c)(1), (2), (4) Date: May 21, 2004

(87) PCT Pub. No.: WO03/045964
PCT Pub. Date: Jun. 5, 2003

(65) Prior Publication Data
US 2005/0010058 A1    Jan. 13, 2005

(30) Foreign Application Priority Data
Nov. 30, 2001 (EP) .................................. 01204624

(51) Int. Cl.
C08F 4/6342 (2006.01)
C07F 17/00 (2006.01)

(52) U.S. Cl. .................. 526/161; 556/53; 502/103; 502/155; 526/160; 526/165; 526/943

(58) Field of Classification Search ............... 556/53; 502/103, 155; 526/160, 165, 161, 943
See application file for complete search history.

(56) References Cited

U.S. PATENT DOCUMENTS

| 2003/0008984 A1 | 1/2003 | Kratzer et al. | 526/127 |
| 2003/0013913 A1 | 1/2003 | Schottek et al. | 564/8 |
| 2003/0149199 A1 | 8/2003 | Schottek et al. | 526/126 |

FOREIGN PATENT DOCUMENTS

| DE | 19962814 | 6/2001 |
| DE | 19962910 | 7/2001 |
| EP | 0129368 | 12/1984 |
| EP | 0633272 | 1/1995 |
| EP | 0697418 | 2/1996 |
| EP | 0846696 | 6/1998 |
| WO | 9102012 | 2/1991 |
| WO | 9200333 | 1/1992 |
| WO | 9532995 | 12/1995 |
| WO | 9822486 | 5/1998 |
| WO | 9921899 | 5/1999 |
| WO | 9936427 | 7/1999 |
| WO | 0121674 | 3/2001 |
| WO | 0144318 | 6/2001 |
| WO | 0148034 | 7/2001 |
| WO | 0162764 | 8/2001 |
| WO | 02083699 | 10/2002 |
| WO | 02100909 | 12/2002 |
| WO | 03014107 | 2/2003 |

OTHER PUBLICATIONS

J. A. Ewen et al., "Chiral *Ansa* Metallocenes with Cp Ring-Fused to Thiophenes and Pyrroles: Syntheses, Crystal Structures, and Isotactic Polypropylene Catalysts;" *J. Am. Soc.*, vol. 123(20), p. 4763-4773 (2001).

*Primary Examiner*—Caixia Lu
(74) *Attorney, Agent, or Firm*—William R Reid; Jarrod N Raphael

(57) ABSTRACT

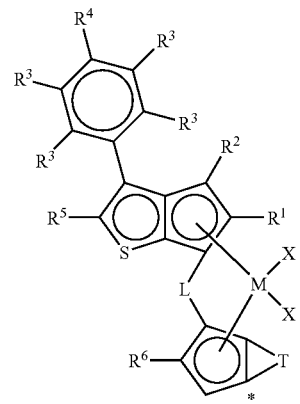

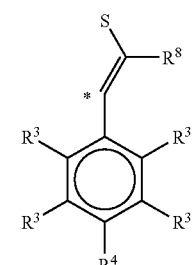

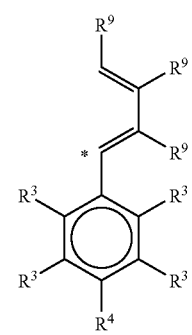

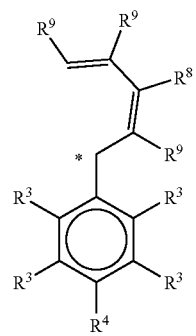

-continued

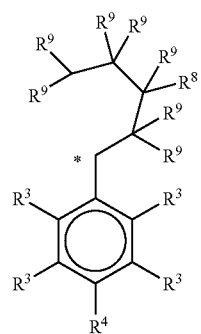

(V)

A metallocene compound of formula (I) wherein M is zirconium, hafnium or titanium; X is hydrogen, halogen, or a hydrocarbyl radical optionally containing heteroatoms; $R^2$, $R^3$, $R^4$ and $R^5$, are hydrogen or hydrocarbyl radicals; $R^6$ is a hydrocarbil radical; L is a divalent bridging group T is a radical of formula (II), (III), (IV) or (V), wherein $R^8$ and $R^9$ are a hydrogen atom or a hydrocarbyl radical. with the proviso that at least one group among $R^1$, $R^5$, $R^6$ and $R^8$ is a group of formula $C(R^{11})_2R^{12}$ wherein $R^{11}$, equal to or different from each other, is an hydrocarbyl radical; and $R^{12}$ is hydrogen or an hydrocarbyl radical. These compounds are fit for the preparation of propylene copolymers.

10 Claims, No Drawings

METALLOCENE COMPOUNDS AND PROCESS FOR THE PREPARATION OF PROPYLENE POLYMERS

This application is the U.S. national phase of International Application PCT/EP02/13552, filed Nov. 28, 2002.

The present invention relates to a new class of metallocene compounds and a process for the preparation of propylene copolymers in the presence of a new class of metallocene catalyst. Propylene polymers have been applied to various uses such as industrial parts, containers, films and non-woven fabrics. However, conventional propylene homopolymers are not always sufficient in transparency, impact resistance and other properties. These properties are often improved by copolymerizing propylene units with others comonomers such as ethylene, 1-butene and other alpha-olefins. In recent years polymers having a narrow molecular weight distribution have been prepared by using metallocene compounds. For example EP 129 368 describes a catalyst system for the polymerization of olefins comprising (a) a bis-cyclopentadienyl coordination complex with a transition metal and (b) an alumoxane. The two cyclopentadienyl groups can be linked by a divalent group.

Among the various development in metallocene catalysts, WO 98/22486 describes a class of metallocenes containing a cyclopentadienyl radical directly coordinating the central metal atom, to which are fused one or more rings containing at least one heteroatom. These metallocenes, in combination with a suitable cocatalyst, are used in the polymerization of olefins, such as propylene. Propylene/ethylene polymer are obtained in WO 01/44318 by using metallocene compounds in which the n ligands are substituted thiopentalenes, but the molecular weights of the obtained polymer are not satisfactory for industrial use. Thus, it would be desirable to have a new class of metallocene compounds able to give propylene copolymers having a higher molecular weight. A novel class of metallocene compounds has now been found, which achieves the above and other results. According to a first aspect, the present invention provides a metallocene compound of formula (I):

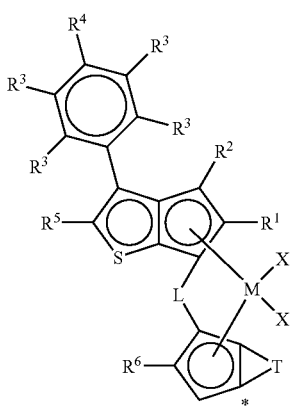

wherein

M is zirconium, hafnium or titanium;

X, equal to or different from each other, is a hydrogen atom, a halogen atom, a R, OR, OR'O, $OSO_2CF_3$, OCOR, SR, $NR_2$ or $PR_2$ group, wherein R is a linear or branched, saturated or unsaturated $C_1$–$C_{20}$-alkyl, $C_3$–$C_{20}$-cycloalkyl, $C_6$–$C_{20}$-aryl, $C_7$–$C_{20}$-allkylaryl, or $C_7$–$C_{20}$-arylalkyl radical, optionally containing one or more heteroatoms belonging to groups 13–17 of the Periodic Table of the Elements; and the R' substituent is a divalent group selected from $C_1$–$C_{40}$-alkylidene, $C_6$–$C_{40}$-arylidene, $C_7$–$C_{40}$-alkylarylidene and $C_7$–$C_{40}$-arylalkylidene radicals; two X can also join to form a $C_4$–$C_{40}$ dienyl ligand, preferably a 1-3 dienyl ligand; examples of $C_1$–$C_{20}$ alkyl radical are methyl, ethyl, n-propyl, isopropyl, n-butyl, i-butyl, s-butyl, t-butyl, n-pentyl, n-hexyl, n-heptyl and n-Octyl radicals, examples of $C_3$–$C_{20}$-cycloalkyl radicals are cyclopentyl and cyclohexyl;

preferably X is a halogen atom, a R, OR'O or OR group; more preferably X is chlorine or methyl;

$R^1$ is a linear or branched, saturated or unsaturated $C_1$–$C_{40}$-alkyl, $C_3$–$C_{40}$-cycloalkyl, $C_6$–$C_{40}$-aryl, $C_7$–$C_{40}$-alkylaryl, or $C_7$–$C_{40}$-arylalkyl radical, optionally containing one or more heteroatoms belonging to groups 13–17 of the Periodic Table of the Elements; preferably $R^1$ is a linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl, or $C_7$–$C_{20}$-arylalkyl radical, optionally containing one or more heteroatoms belonging to groups 13–17 of the Periodic Table of the Elements; more preferably $R^1$ is a linear or branched, saturated or unsaturated $C_1$–$C_{20}$-alkyl radical;

$R^2$, $R^3$, $R^4$ and $R^5$, equal to or different from each other, are hydrogen atoms, halogen atoms or linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl, or $C_7$–$C_{20}$-arylalkyl radicals, optionally containing one or more heteroatoms belonging to groups 13–17 of the Periodic Table of the Elements; preferably $R^2$ and $R^3$ are hydrogen; preferably at least one $R^4$ is a group $—C(R^7)_3$, wherein $R^7$, equal to or different from each other, is a linear or branched, saturated or unsaturated $C_1$–$C_{20}$-alkyl radical; preferably a linear or branched saturated or unsaturated $C_1$–$C_{16}$-alkyl radical; and preferably $R^5$ is a linear or branched, saturated or unsaturated $C_1$–$C_{20}$-alkyl radical;

$R^6$ is a linear or branched, saturated or unsaturated $C_1$–$C_{40}$-alkyl, $C_3$–$C_{40}$-cycloalkyl, $C_6$–$C_{40}$-aryl, $C_7$–$C_{40}$-alkylaryl, or $C_7$–$C_{40}$-arylalkyl radical, optionally containing one or more heteroatoms belonging to groups 13–17 of the Periodic Table of the Elements; preferably $R^6$ is a linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl, or $C_7$–$C_{20}$-arylalkyl radical, optionally containing one or more heteroatoms belonging to groups 13–17 of the Periodic Table of the Elements; more preferably $R^6$ is a linear or branched, saturated or unsaturated $C_1$–$C_{20}$-alkyl radical;

L is a divalent bridging group selected from $C_1$–$C_{20}$ alkylidene, $C_3$–$C_{20}$ cycloalkylidene, $C_6$–$C_{20}$ arylidene, $C_7$–$C_{20}$ alkylarylidene, or $C_7$–$C_{20}$ arylalkylidene radicals optionally containing heteroatoms belonging to groups 13–17 of the Periodic Table of the Elements, and silylidene radical containing up to 5 silicon atoms such as $SiMe_2$, $SiPh_2$; preferably L is selected from the group consisting of is $Si(CH_3)_2$, $SiPh_2$, $SiPhMe$, $SiMe(SiMe_3)$, $CH_2$, $(CH_2)_2$, $(CH_2)_3$ and $C(CH_3)_2$;

T is a divalent radical of formula (II), (III), (IV) or (V):

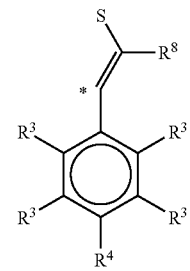

(II)

-continued

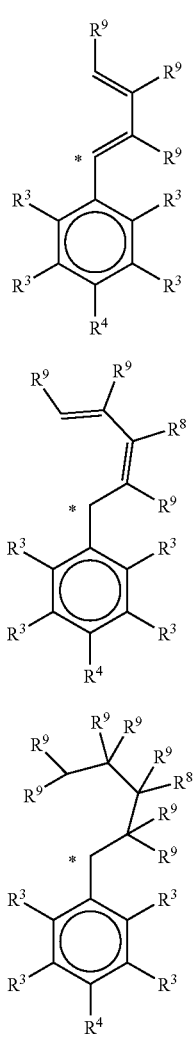

wherein
the atom marked with the symbol * bonds the atom marked with the same symbol in the compound of formula (I);
$R^3$ and $R^4$ have the meaning previously described;
$R^8$ is a hydrogen atom or a linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl, or $C_7$–$C_{20}$-arylalkyl radical, optionally containing one or more heteroatoms belonging to groups 13–17 of the Periodic Table of the Elements; preferably $R^8$ is hydrogen or a linear or branched, saturated or unsaturated $C_1$–$C_{20}$-alkyl;
$R^9$, equal to or different from each other, is a hydrogen atom or a linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl, or $C_7$–$C_{20}$-arylalkyl radical, optionally containing one or more heteroatoms belonging to groups 13–17 of the Periodic Table of the Elements; preferably $R^9$ are hydrogen or a linear or branched, saturated or unsaturated $C_1$–$C_{20}$-alkyl;
with the proviso that at least one group between $R^1$ and $R^6$ is a group of formula $C(R^{11})_2 R^{12}$ wherein $R^{11}$, equal to or different from each other, is a linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl, or $C_7$–$C_{20}$-arylalkyl radical, optionally containing one or more heteroatoms belonging to groups 13–17 of the Periodic Table of the Elements; or two $R^{11}$ groups can join to form a $C_3$–$C_{20}$ saturated or unsaturated ring; preferably $R^{11}$ is a linear or branched, saturated or unsaturated $C_1$–$C_{20}$-alkyl radical; more preferably $R^{11}$ is a linear or branched, saturated or unsaturated $C_1$–$C_8$-alkyl radical; $R^{12}$ is a hydrogen atom or a linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl, or $C_7$–$C_{20}$-arylalkyl radical, optionally containing one or more heteroatoms belonging to groups 13–17 of the Periodic Table of the Elements; preferably $R^{12}$ is hydrogen.

Preferably the metallocene compound of formula (I) is in the racemic form.

Preferred radicals of group T are those of formula (II) and (III).

Non limitative examples of compound of formula (I) are:

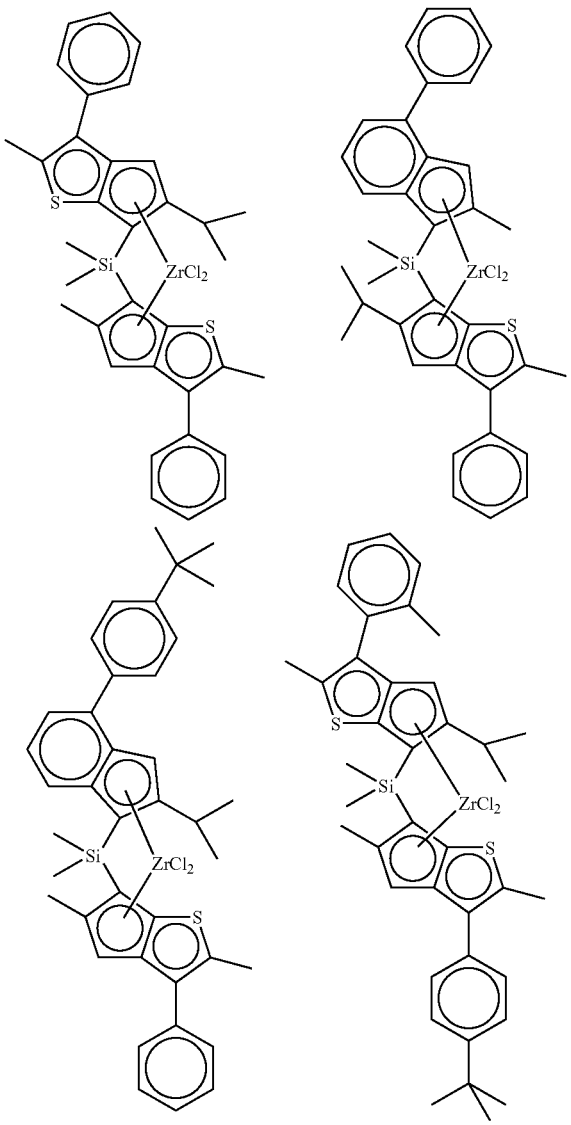

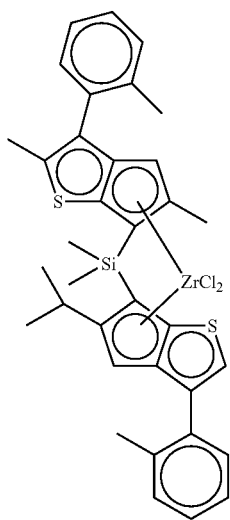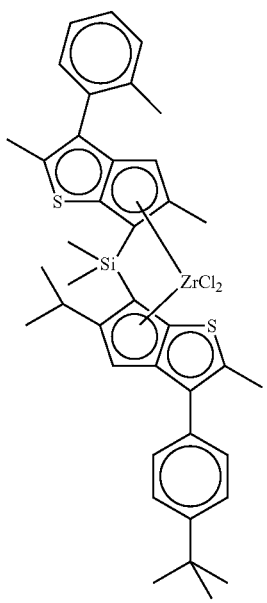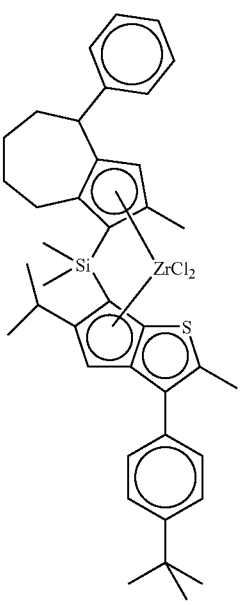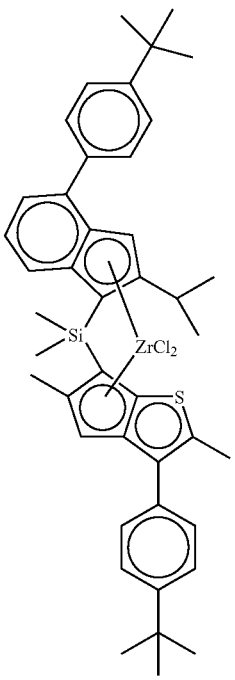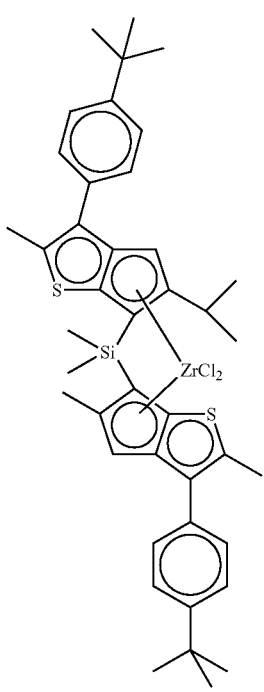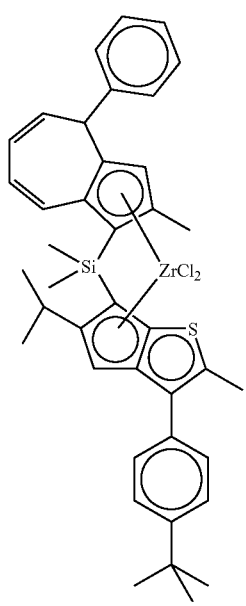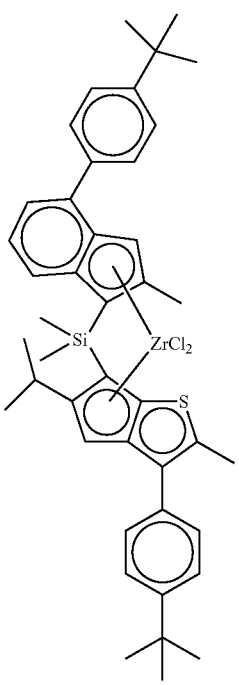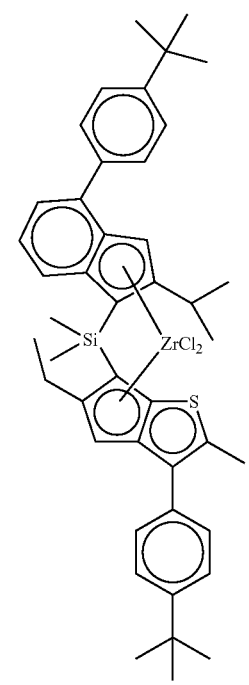

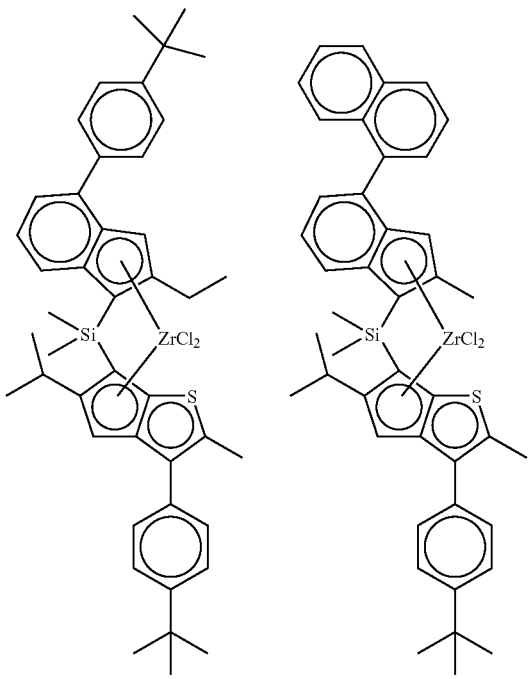

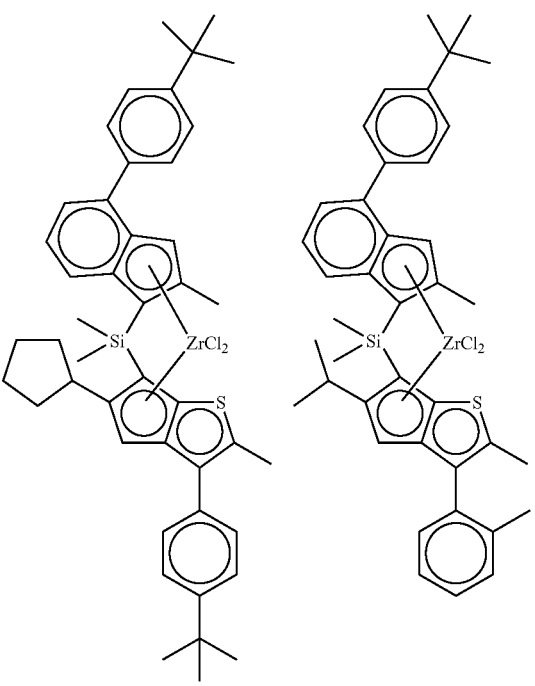

Compounds of formula (I) can be prepared by contacting a ligand of formula (Ia)

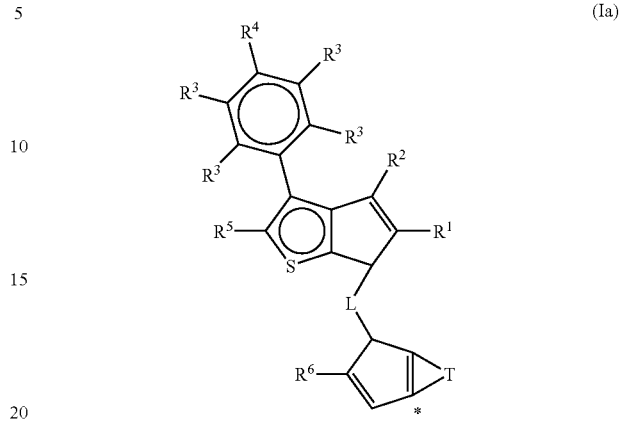

or one of its double bonds isomers, wherein $R^1$, $R^2$, $R^3$, $R^4$, $R^5$, $R^6$ T and L have been described above; with at least two equivalents of a base, selected from the group consisting of metallic sodium and potassium, sodium and potassium hydroxide and an organolithium compound, such as butyl-lithium and then contacting the obtained salt with a compound of formula $MX_4$, wherein M and X have been described above.

Alternative processes for obtaining the compounds of formula (I) are described in WO 02/083699 and WO 99/36427.

The ligand of formula (Ia) can be obtained according to a process comprising the following steps:

a) contacting a compound of formula (Ib):

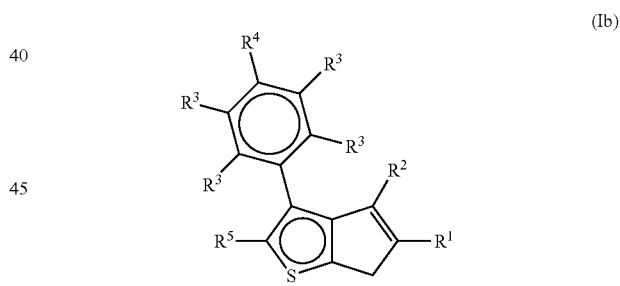

wherein $R^1$, $R^2$, $R^3$, $R^4$ and $R^5$ are defined as above;
with a base selected from the group consisting of metallic sodium and potassium, sodium and potassium hydroxide and an organolithium compound, wherein the molar ratio between the compound of the formula (Ib) and said base is at least 1:1;

b) contacting the obtained anionic compounds with a compound of formula (Ic):

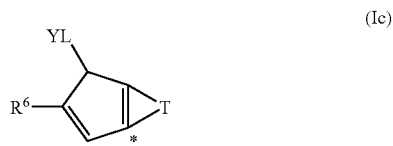

wherein L, $R^6$ and T are defined as above and Y is a halogen radical selected from the group consisting of chlorine, bromine and iodine, preferably Y is chlorine or bromine.

Compounds of formula (Ib) and (Ic) are known in the art. In particular, compounds of formula (Ib) and compounds of formula (Ic) when T is a radical of formula (II) can be prepared according to the process described in WO01/44318 and PCT/EP02/07680. Those compounds of formula (Ic) in which T is a radical of formula (III) can be prepared according to WO 01/48034. Those compound of formula (Ic) in which the radical T has formulas (IV), or (V) can be prepared according to EP 846 696 and EP 697 418.

Preferred metallocene of formula (I) are the compounds in which at least one $R^4$ is a $—C(R^7)_3$ group, wherein $R^7$ is described as above.

A further object of the present invention is a process for the preparation of propylene copolymers having a propylene derived units content of up to 50% by weight, meaning comprised between a value lower than 100% by weight and 50% by weight. In other words, the content of propylene derived units is at least 50% by weight, being generally comprised between 99.1% and 50% by weight; preferably between 99.5% and 80% by weight; more preferably between 99.5% and 90% by weight. Said process comprises the step of contacting, under polymerization conditions, propylene with one or more alpha olefins of formula $CH_2=CHA$, wherein A is hydrogen or a $C_2–C_{20}$ alkyl radical, in the presence of a catalyst system obtainable by contacting:

a) a metallocene compound of formula (I) as described above;

b) an alumoxane or a compound able to form an alkylmetallocene cation; and optionally c) an organo aluminum compound.

Alumoxanes used as component b) can be obtained by reacting water with an organo-aluminium compound of formula $H_jAlU_{3-j}$ or $H_jAl_2U_{6-j}$, where the U substituents, same or different, are hydrogen atoms, $C_1–C_{20}$-alkyl, $C_3–C_{20}$-cyclalkyl, $C_6–C_{20}$-aryl, $C_7–C_{20}$-alkylaryl or $C_7–C_{20}$-arylalkyl radical, optionally containing silicon or germanium atoms, with the proviso that at least one U is different from halogen, and j ranges from 0 to 1, being also a non-integer number. In this reaction the molar ratio of Al/water is preferably comprised between 1:1 and 100:1. The molar ratio between aluminium and the metal of the metallocene generally is comprised between about 10:1 and about 30000:1, preferably between about 100:1 and about 5000:1. The alumoxanes used in the catalyst according to the invention are considered to be linear, branched or cyclic compounds containing at least one group of the type:

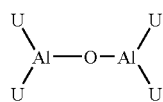

wherein the substituents U, same or different, are described above.

In particular, alumoxanes of the formula:

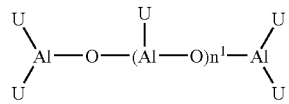

can be used in the case of linear compounds, wherein $n^1$ is 0 or an integer of from 1 to 40 and the substituents U are defined as above, or alumoxanes of the formula:

can be used in the case of cyclic compounds, wherein $n^2$ is an integer from 2 to 40 and the U substituents are defined as above.

Examples of alumoxanes suitable for use according to the present invention are methylalumoxane (MAO), tetra-(isobutyl)alumoxane (TIBAO), tetra-(2,4,4-trimethyl-pentyl)alumoxane (TIOAO), tetra-(2,3-dimethylbutyl)alumoxane (TDMBAO) and tetra-(2,3,3-trimethylbutyl)alumoxane (TTMBAO).

Particularly interesting cocatalysts are those described in WO 99/21899 and in WO01/21674 in which the alkyl and aryl groups have specific branched patterns.

Non-limiting examples of aluminium compounds according to WO 99/21899 and WO01/21674 are:
tris(2,3,3-trimethyl-butyl)aluminium, tris(2,3-dimethyl-hexyl)aluminium, tris(2,3-dimethyl-butyl)aluminium, tris(2,3-dimethyl-pentyl)aluminium, tris(2,3-dimethyl-heptyl)aluminium, tris(2-methyl-3-ethyl-pentyl)aluminium, tris(2-methyl-3-ethyl-hexyl)aluminium, tris(2-methyl-3-ethyl-heptyl)aluminium, tris(2-methyl-3-propyl-hexyl) aluminium, tris(2-ethyl-3-methyl-butyl)aluminium, tris (2-ethyl-3-methyl-pentyl)aluminium, tris(2,3-diethyl-pentyl)aluminium, tris(2-propyl-3-methyl-butyl) aluminium, tris(2-isopropyl-3-methyl-butyl)aluminium, tris(2-isobutyl-3-methyl-pentyl)aluminium, tris(2,3,3-trimethyl-pentyl)aluminium, tris(2,3,3-trimethyl-hexyl)aluminium, tris(2-ethyl-3,3-dimethyl-butyl)aluminium, tris (2-ethyl-3,3-dimethyl-pentyl)aluminium, tris(2-isopropyl-3,3-dimethyl-butyl)aluminium, tris(2-trimethylsilyl-propyl)aluminium, tris(2-methyl-3-phenyl-butyl)aluminium, tris(2-ethyl-3-phenyl-butyl)aluminium, tris(2,3-dimethyl-3-phenyl-butyl)aluminium, tris(2-phenyl-propyl)aluminium, tris[2-(4-fluoro-phenyl)-propyl] aluminium, tris[2-(4-chloro-phenyl)-propyl]aluminium, tris[2-(3-isopropyl-phenyl)-propyl]aluminium, tris(2-phenyl-butyl)aluminium, tris(3-methyl-2-phenyl-butyl) aluminium, tris(2-phenyl-pentyl)aluminium, tris[2-(pentafluorophenyl)-propyl]aluminium, tris[2,2-diphenyl-ethyl]aluminium and tris[2-phenyl-2-methyl-propyl] aluminum, as well as the corresponding compounds wherein one of the hydrocarbyl groups is replaced with a hydrogen atom, and those wherein one or two of the hydrocarbyl groups are replaced with an isobutyl group.

Amongst the above aluminium compounds, trimethylaluminium (TMA), triisobutylaluminium (TIBAL), tris(2,4,4-trimethyl-pentyl)aluminium (TIOA), tris(2,3-dimethylbutyl)aluminium (TDMBA) and tris(2,3,3-trimethylbutyl) aluminium (TTMBA) are preferred.

Non-limiting examples of compounds able to form an alkylmetallocene cation are compounds of formula $D^+E^-$; wherein $D^+$ is a Brønsted acid, able to donate a proton and to react irreversibly with a substituent X of the metallocene of formula (I) and $E^-$ is a compatible anion, which is able to stabilize the active catalytic species originating from the reaction of the two compounds, and which is sufficiently labile to be able to be removed by an olefinic monomer. Preferably, the anion $E^-$ comprises of one or more boron atoms. More preferably, the anion $E^-$ is an anion of the formula $BAr_4^{(-)}$, wherein the substituents Ar which can be identical or different are aryl radicals such as phenyl, pentafluorophenyl or bis(trifluoromethyl)phenyl. Tetrakis-pentafluorophenyl borate is particularly preferred examples of these compounds are described in WO 91/02012. Moreover, compounds of the formula $BAr_3$ can conveniently be used. Compounds of this type are described, for example, in the published International patent application WO 92/00333. Other examples of compounds able to form an alkylmetallocene cation are compounds of formula $BAr_3P$ wherein P is a substituted or unsubstituted pyrrol radicals. These compounds are described in WO01/62764. Compounds containing boron atoms can be conveniently supported according to the description of DE-A-19962814 and DE-A-19962910. All these compounds containing boron atoms can be used in a molar ratio between boron and the metal of the metallocene comprised between about 1:1 and about 10:1; preferably 1:1 and 2.1; more preferably about 1:1.

Non limiting examples of compounds of formula $D^+E^-$ are:
Triethylammoniumtetra(phenyl)borate,
Tributylammoniumtetra(phenyl)borate,
Trimethylammoniumtetra(tolyl)borate,
Tributylammoniumtetra(tolyl)borate,
Tributylammoniumtetra(pentafluorophenyl)borate,
Tributylammoniumtetra(pentafluorophenyl)aluminate,
Tripropylammoniumtetra(dimethylphenyl)borate,
Tributylammoniumtetra(trifluoromethylphenyl)borate,
Tributylammoniumtetra(4-fluorophenyl)borate,
N,N-Dimethylaniliniumtetra(phenyl)borate,
N,N-Diethylaniliniumtetra(phenyl)borate,
N,N-Dimethylaniliniumtetrakis(pentafluorophenyl)boratee,
N,N-Dimethylaniliniumtetrakis(pentafluorophenyl)aluminate,
Di(propyl)ammoniumtetrakis(pentafluorophenyl)borate,
Di(cyclohexyl)ammoniumtetrakis(pentafluorophenyl)borate,
Triphenylphosphoniumtetrakis(phenyl)borate,
Triethylphosphoniumtetrakis(phenyl)borate,
Diphenylphosphoniumtetrakis(phenyl)borate,
Tri(methylphenyl)phosphoniumtetrakis(phenyl)borate,
Tri(dimethylphenyl)phosphoniumtetrakis(phenyl)borate,
Triphenylcarbeniumtetrakis(pentafluorophenyl)borate,
Triphenylcarbeniumtetrakis(pentafluorophenyl)aluminate,
Triphenylcarbeniumtetrakis(phenyl)aluminate,
Ferroceniumtetrakis(pentafluorophenyl)borate,
Ferroceniumtetrakis(pentafluorophenyl)aluminate.
Triphenylcarbeniumtetrakis(pentafluorophenyl)borate,
N,N-Dimethylaniliniumtetrakis(pentafluorophenyl)borate.

Organic aluminum compounds used as compound c) are those of formula $H_jAlU_{3-j}$ or $H_jAl_2U_{6-j}$ described above.

The catalysts of the present invention can also be supported on an inert carrier. This is achieved by depositing the metallocene compound a) or the product of the reaction thereof with the component b), or the component b) and then the metallocene compound a) on an inert support such as, for example, silica, alumina, Al—Si, Al—Mg mixed oxides, magnesium halides, styrene/divinylbenzene copolymers, polyethylene or polypropylene. The supportation process is carried out in an inert solvent such as hydrocarbon for example toluene, hexane, pentane or propane and at a temperature ranging from 0° C. to 100° C., preferably the process is carried out at room temperature. A suitable class of supports which can be used is that constituted by porous organic supports functionalized with groups having active hydrogen atoms. Particularly suitable are those in which the organic support is a partially crosslinked styrene polymer. Supports of this type are described in European application EP-633 272.

Another class of inert supports particularly suitable for use according to the invention is that of polyolefin porous prepolymers, particularly polyethylene. A farther suitable class of inert supports for use according to the invention is that of porous magnesium halides such as those described in International application WO 95/32995. The solid compound thus obtained, in combination with the further addition of the alkylaluminium compound either as such or prereacted with water if necessary, can be usefully employed in the gas-phase polymerization.

According to the process of the present invention propylene and one or more alpha olefins of formula $CH_2=CHA$ wherein A is hydrogen or a $C_2-C_{20}$ alkyl radical, can be polymerized obtaining copolymers having an high molecular weight. Non limitative examples of alpha-olefins of formula $CH_2=CHA$ are: ethylene, 1-butene, 1-hexene, 1-octene and 4-methyl-1-pentene, preferred alpha olefins are ethylene and 1-butene. The content of the comonomer can vary from 0.1% to 50% by weight, preferably from 0.5% to 20% by weight, more preferably from 0.5% to 10% by weight. The process for the polymerization of olefins according to the invention can be carried out in the liquid phase in the presence or absence of an inert hydrocarbon solvent, or in the gas phase. The hydrocarbon solvent can either be aromatic such as toluene, or aliphatic such as propane, hexane, heptane, isobutane or cyclohexane. The polymerization temperature is generally comprised between −100° C. and +100° C. and, particularly between 10° C. and +90° C. The polymerization pressure is generally comprised between 0.5 and 100 bar. The lower the polymerization temperature, the higher are the resulting molecular weights of the polymers obtained. The polymerization yields depend on the purity of the metallocene compound of the catalyst. The metallocene compounds obtained by the process of the invention can therefore be used as such or can be subjected to purification treatments. The components of the catalyst can be brought into contact with each other before the polymerization. The pre-contact concentrations are generally between 0.1 and $10^{-8}$ mol/l for the metallocene component a), while they are generally between 2 and $10^{-8}$ mol/l for the component b). The pre-contact is generally effected in the presence of a hydrocarbon solvent and, if appropriate, of small quantities of monomer. In the pre-contact it is also possible to use a non-polymerizable olefin such as isobutene, 2-butene and the like. The molecular weight distribution can be varied by using mixtures of different metallocene compounds or by carrying out the polymerization in several stages which differ as to the polymerization temperature and/or the concentrations of the molecular weight regulators and/or the monomers concentration. Moreover by carrying out the polymerization process by using a combination of two different metallocene compounds of formula (I) a polymer endowed with a broad melting is produced. By using the metallocene compounds of formula (I) it is possible to obtain propylene copolymers, especially propylene ethylene copolymers endowed with a high molecular weight as shown by their intrinsic viscosity (I.V.) values, that makes the metallocene compounds of formula (I) useful for application on industrial scale. The intrinsic viscosity values are generally higher than 0.5 dL/g preferably they are between from 1.5 to 10 dL/g. The following examples are given for illustrative purpose and do not intend to limit the invention.

EXAMPLES

General Materials and Procedure

All syntheses were performed under a nitrogen atmosphere in pre-dried glassware unless stated otherwise. Solvents for air-sensitive compounds were purified as follows: THF, ether, and toluene were distilled from sodium/benzophenone, pentane was distilled from sodium/benzophenone/tri-glyme, dichloromethane was distilled from $CaH_2$ and stored over 4A sieves.

MS. Mass spectra of organic intermediates were measured with an HP 6890 series GC equipped with a 5973 mass selective detector.

Synthesis of Ligand

Synthesis of 5-Isopropyl-2-methyl-3-phenyl-6H-cyclopenta[b]thiophene a) 3-methyl-1-(5-methyl-4-phenyl-(2-thienyl))butan-1-one A solution of 2-methyl-3-phenylthiophene (102.8 g, 0.590 mol) and 3-methylbutanoyl chloride (72.3 g, 0.600 mol) in 60 mL of dichloromethane was added dropwise to a 1 M solution of $SnCl_4$ in dichloromethane (640 mL, 0.640 mol) at 0° C. The solution was stirred for 6 h at room temperature then poured slowly into water (500 mL). The organic fraction was separated, washed with a saturated aqueous solution of $NaHCO_3$, brine solution, and dried ($MgSO_4$). Solvents were removed on a rotoevaporator and the product was distilled (145° C., ~0.03 torr). Yield=132.9 g. $^1$H-NMR δ ($CDCl_3$): 7.61 (s, 1H), 7.3–7.5 (m, 5H), 2.72 (d, 2H), 2.52 (s, 3H), 2.3 (m, 1H), 1.0 (d, 6H). EIMS: m/z (%) 258 ($M^+$, 38), 243 (25), 216 (69), 201 (100), 174 (11), 129 (25), 115 (11).

b) 2-(isopropyl)-1-(5-methyl-4-phenyl(2-thienyl))prop-2-en-1-one.

3-methyl-1-(5-methyl-4-phenyl-(2-thienyl))butan-1-one (106 g, 0.411 mol), urotropin (161.2 g, 1.15 mol), and acetic anhydride (151.1 g, 1.48 mol) were mixed in a 1 L flask, sparged with nitrogen, and stirred for 24 h at 110° C. The dark mixture was cooled to 70° C. and poured into 700 mL of a 2 N aqueous solution of NaOH. The organic fraction was extracted with 50/50 (v/v) dichloromethane/hexane (3×250 mL), washed with 1 N HCl, saturated aqueous solution of $NaHCO_3$, and dried ($MgSO_4$). Evaporation of solvents gave 98 g of crude product (70% product by GC/MS) used without further purification. $^1$H-NMR δ ($CDCl_3$): 7.5 (s, 1H), 7.2–7.38 (m, 5H), 5.6 (s, 1H), 5.45 (s, 1H), 2.9 (m, 1H), 2.41 (s, 3H), 1.05 (d, 6H). EIMS: m/z (%) 270 ($M^+$, 65), 255 (100), 237 (11), 201 (89), 171 (11), 129 (38).

c) 2-methyl-5-(isopropyl)-3-phenyl-4,5-dihydrocyclopenta[2,1-b]thiophen-6-one.

A mixture of 2-(isopropyl)-1-(5-methyl-4-phenyl(2-thienyl))prop-2-en-1-one (98 g crude product) and Eaton's reagent (200 mL) was heated to 90° C. with stirring. After 10 minutes, the reaction mixture was poured slowly into water (500 mL). The product was extracted with dichloromethane, washed with a saturated aqueous solution of $NaHCO_3$, and dried ($MgSO_4$). Rotoevaporation of solvent gave 98 g of crude product (~70% product by GC/MS). A portion of the product was further refined by chromatography on silica. $^1$H-NMR δ ($CDCl_3$): 7.15–7.4 (m, 5H), 2.7 (m, 2H), 2.5 (m, 1H), 2.38 (s, 3H), 2.3 (m, 1H), 0.9 (d, 3H). EIMS: m/z (%) 270 ($M^+$, 10), 255 (4), 228 (100), 213 (5), 195 (5), 184 (10), 165 (7), 152 (6).

d) 5-Isopropyl-2-methyl-3-phenyl-6H-cyclopenta[b]thiophene.

A solution of 2-methyl-5-(isopropyl)-3-phenyl-4,5-dihydrocyclopenta[2,1-b]thiophen-6-one (18.5 g, 0.068 mol) in 80 mL of ether was treated with 40 mL of an ether solution of $LiAlH_4$ (1 M, 0.04 mol). After sting for 12 h, water (~20 mL) was added cautiously and the mixture was filtered through celite. The filter pad was washed with dichloromethane (3×100 mL) and the combined organic fractions were dried ($MgSO_4$). Solvents were evaporated and the residue was dissolved in 150 mL of toluene. p-TSA (1.0 g) was added and the mixture was stirred at 80° C. for 2 h. After cooling, the mixture was washed with a saturated aqueous solution of $NaHCO_3$, brine solution, and dried ($MgSO_4$). Evaporation of solvent gave 18.1 g of product (93% purity by GC/MS). $^1$H-NMR δ ($CD_2Cl_2$): (major isomer) 7.3–7.5 (m, 5H), 6.48 (s, 1H), 3.2 (s, 2H), 2.8 (m, 1H), 2.5 (s, 3H), 1.22 (d, 6H). EIMS: m/z (%) 254 ($M^+$, 55), 239 (100), 224 (25), 211 (5), 191 (5), 178 (9), 165 (7).

Preparation of Metallocene Compounds $Me_2Si(2,5-Me_2-3-Ph-cyclopento[2,3-b]thiophen-6-yl)_2 ZrCl_2$ (C-1)

$Me_2Si(2,5-Me_2-3-Ph-cyclopento[2,3-b]thiophen-6-yl)_2 ZrCl_2$ (C-1) was synthesized according to example 1 of WO01/44318.

Example 1

{$Me_2Si(2,5-Me2-3-Ph-cyclopento[2,3-b]thiophen-6-yl)(2-Me-5-iPr-3-Ph-cyclopento[2,3-b]thiophen-6-yl)$}$ZrCl_2$ (A-1)

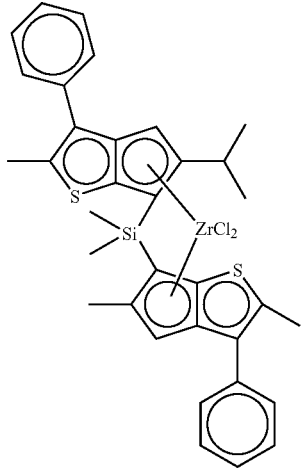

a) 2,5-dimethyl-3-phenyl-4-hydrocyclopenta[2,1-b]thiophene 2,5-dimethyl-3-phenyl-4-hydrocyclopenta[2,1-b]thiophene was prepared by the literature method (see J. A. Ewen, et. al., *J. Am. Chem. Soc.*, 2001, 123, 4763).

b) (2,5-$Me_2$-3-Ph-6-hydrocyclopenta[2,3-b]thiophen-6-yl) (2-Me-5-iPr-3-Ph-6-hydrocyclopenta[2,3-b]thiophen-6-yl) SiMe2.

2-methyl-5-(isopropyl)-3-phenyl-4-hydrocyclopenta[2,1-b]thiophene (7.37 g, 0.029 mol) was dissolved in 60 mL of ether and treated with 12 mL of Butyllithium in hexanes (2.5 M, 0.030 mol) at −78° C. After stirring at room temperature for 12 h, the mixture was cooled to −78° C. and 5.7 g (0.44 mol) of dichlorodimethylsilane were syringed into the flask. The reaction mixture was warmed to room temperature, stirred overnight, filtered, and volatiles removed from the filtrate in vacuo. The residue was redissolved in 60 mL of THF, cooled to −78° C., and treated with a THF solution (60 mL) of the lithium salt of 2,5-dimethyl-3-phenyl-4-hydrocyclopenta[2,1-b]thiophene (0.029 mol). After stirring for 24 h at 60° C., the reaction mixture was washed with water, dried (MgSO$_4$), and evaporated to an oil. The crude product was chromatographed on silica (10% CH$_2$Cl$_2$ in hexanes). 9.5 g of the dimethylsilyl bridged ligand were recovered. EIMS: m/z (%) 536 (M$^+$, 30), 311 (85), 283 (100), 252 (20), 221 (12), 195 (17), 178 (21).

c) Me$_2$Si(2,5-Me$_2$-3-Ph-cyclopento[2,3-b]thiophen-6-yl)(2-Me-5-iPr-3-cyclopento[2,3-b]thiophen-6-yl)}ZrCl$_2$ 5.4 g (0.010 mol) of the ligand (2,5-Me$_2$-3-Ph-6-hydrocyclopenta[2,3-b]thiophen-6-yl)(2-Me-5-iPr-3-Ph-6-hydrocyclopenta[2,3-b]thiophen-6-yl)SiMe2 were dissolved in 80 mL of ether, treated with 8.4 mL of butyllithium in hexanes (2.5 M, 0.021 mol), and stirred at room temperature for 16 h. Solvents were removed from the orange slurry in vacuo, ZrCl$_4$ (2.33 g, 0.010 mol) was added, and the mixture was stirred overnight in 80 mL of hexane containing 5 mL of ether. The yellow slurry was filtered through a closed frit giving 3.3 g of yellow solids on the frit. The filtrate was evaporated in vacuo to a yellow powder (2.8 g). A sample of the rac isomer (0.7 g) was obtained by washing the filtrate product with acetone. $^1$H-NMR δ (CD$_2$Cl$_2$): 7.3–7.6 (m, 10H), 6.65 (s, 1H), 6.58 (s, 1H), 3.3 (m, 1H), 2.58 (s, 3H), 2.55 (s, 3H), 2.3 (s, 3H), 1.0–1.25 (d, 3H; d, 3H; s, 3H; s, 3H).

Example 2

Synthesis of {Me$_2$Si(2-Me-5-iPr-3-Ph-cyclopento[2,3-b]thiophen-6-yl)(2-Me-4-Ph-inden-6-yl}ZrCl$_2$. (A-2)

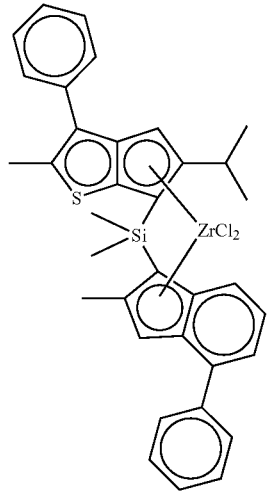

a) (2-Me-4-Ph-inden-1-yl)(2-Me-5-iPr-3-Ph-6-hydrocyclopenta[2,3-b]thiophen-6-yl)SiMe2.

2-Methyl-4-phenylindene (5.77 g, 0.028 mol) was dissolved in 60 mL of ether and treated with 12 mL of Butyllithium in hexanes (2.5 M, 0.030 mol) at −78° C. After stirring at room temperature for 12 h, the mixture was cooled to −78° C. and 5.7 g (0.44 mol) of dichlorodimethylsilane were syringed into the flask. The reaction mixture was warmed to room temperature, stirred for 10 h, filtered, and volitles removed from the filtrate in vacuo. The residue was redissolved in 60 mL of THF, cooled to −78° C., and treated with a THF solution (60 mL) of the lithium salt of 2-methyl-5-(isopropyl)-3-phenyl-4-hydrocyclopenta[2,1-b]thiophene (0.028 mol). After stirring for 24 h at 60° C., the reaction mixture was washed with water, dried (MgSO$_4$), and evaporated to an oil. The crude product was chromatographed on silica (10% CH$_2$Cl$_2$ in hexanes). 9.9 g of the dimethylsilyl bridged ligand were recovered. EIMS: m/z (%) 516 (M$^+$, 20), 311 (100), 291 (3), 263 (35), 238 (6), 221 (7), 203 (8), 181 (6).

b) {Me$_2$Si(2-Me-5-iPr-3-Ph-cyclopento[2,3-b]thiophen-6-yl)(2-Me-4-Ph-inden-1-yl}ZrCl$_2$.

6.6 g (0.012 mol) of the ligand (2-Me-4-Ph-inden-1-yl) (2-Me-5-iPr-3-Ph-6-hydrocyclopenta[2,3-b]thiophen-6-yl) SiMe2 were dissolved in 100 mL of ether, treated with 9.6 mL of butyllithium in hexanes (2.5 M, 0.024 mol), and stirred at room temperature for 16 h. Solvents were removed from the orange slurry in vacuo, ZrCl$_4$ (2.7 g, 0.012 mol) was added, and the mixture was stirred for 18 h in 80 mL of hexane containing 5 mL of ether. The yellow solids were collected on a closed frit and dried in vacuo (8.5 g). A portion of the crude product (3.0 g) was dissolved in dichloromethane, filtered through a plug of celite, and concentrated. 0.3 g of the rac isomer were recovered from the concentrate. $^1$H-NMR δ (CD$_2$Cl$_2$): 7.7 (t, 3H), 7.3–7.5 (m. 9H), 7.15 (t, 1H), 7.0 (s, 1H), 6.55 (s, 1H), 3.2 (m, 1H), 2.56 (s, 3H), 2.4 (s, 3H), 1.3 (s, 3H), 1.08 (s, 3H), 1.05 (d, 3H), 0.95 (d, 3H). An additional 1 g of r/m mixture was precipitated from the concentrate by adding a small portion of hexane. After filtration, further evaporation of the concentrate yielded 0.8 g of the meso isomer. $^1$H-NMR δ (CD$_2$Cl$_2$): 7.2–7.8 (m, 12H), 6.95 (t, 1H), 6.9 (s, 1H), 6.5 (s, 1H), 3.1 (m, 1H), 2.40 (s, 3H), 2.38 (s, 3H), 1.4 (d, 3H), 1.38 (s, 2H), 1.25 (s, 3H), 1.20 (d, 3H).

Example 3

Synthesis of {Me$_2$Si(4-(4-tert-Butyl-phenyl)-2-isopropyl-inden-1-yl) (2,5-dimethyl-3-phenyl-cyclopento[2,3-b]thiophen-6-yl)}ZrCl$_2$. (A-3)

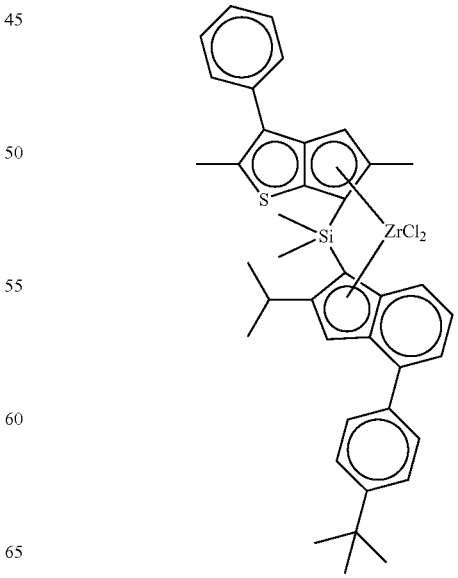

a) (4-(4-tert-Butyl-phenyl)-2-isopropyl-1H-inden-1-yl)(2,5-dimethyl-3-phenyl-6H-cyclopenta[b]thiophen-6-yl)-dimethyl-silane.

To a solution containing 1.52 g (6.7 mmol) 2,5-dimethyl-3-phenyl-4-hydrocyclopenta[2,1-b]thiophene dissolved in 100 ml diethyl ether was added a 2.5 M solution of n-butyllithium in hexane (6.7 mmol, 2.7 ml). The reaction mixture was stirred for 5 h., then solvents were removed in vacuo. The solids were repeatedly washed with dry pentane then dissolved in 40 ml THF. In a separate flask, 2.2 g (6.7 mmol) of chloro-(2-isopropyl-4-(4-tert-butyl-phenyl)-1H-inden-1-yl)-dimethyl-silane was dissolved in 30 ml of THF and stirred at −78° C. Drop-wise, the anion solution (prepared above) was added. The flask was allowed to warn to room temperature and stirring was continued for 18 h then the reaction mixture was quenched with water. The organic fraction was washed with water, dried over magnesium sulfate, filtered, then solvents removed in vacuo. Yield: 3.41 g of yellow oil.

The oil was chromatographed on silica using hexane; 1.1 g of white solid were recovered (Yield: 28%), $^1$H NMR (CD$_2$Cl$_2$): δ 7.0–7.8 (m, 12H), 6.9 (d, 1H), 6.55 (d, 1H), 4.1–4.2 (m, 1 H), 3.7 (d, 0.7 H), 3.3 (m, 0.3H), 2.8 (m, 1H), 2.55–2.7 (m, 3H), 2.1–2.4 (m, 3H), 1.1–1.5 (m, 15H), 0.0 to −0.3 (m, 6H).

b) {Me$_2$Si(4-(4-tert-Butyl-phenyl)-2-isopropyl-inden-1-yl)(2,5-dimethyl-3-phenyl-cyclopento[2,3-b]thiophen-6-yl)}ZrCl$_2$.

To a solution containing 0.75 g (1.3 mmol) [4-(4-tert-Butyl-phenyl)-2-isopropyl-1H-inden-1-yl]-(2,5-dimethyl-3-phenyl-6H-cyclopenta[b]thiophen-6-yl)-dimethyl-silane dissolved in 70 ml diethyl ether was added a 2.5 M solution of n-butyllithium in hexane (2.6 mmol, 1.04 ml). The reaction mixture was stirred for 18 h, then 0.3 g (1.3 mmol) of zirconium tetrachloride was slowly added as a dry powder. Stirring was continued for 8 h, then the mixture was filtered and solvents were removed in vacuo.

Yield: 0.75 g (77%).

The yellow solids collected in this fashion were slurried in pentane, then filtered; solvents were removed from ether fraction in vacuo.

The ether soluble pentane soluble fraction (ESPS: 0.35 g) and the ether soluble pentane insoluble fraction (ESPI: 0.24 g) were recovered as dry free flowing powders.

ESPS (78% meso): $^1$H NMR (CD$_2$Cl$_2$): δ 6.8–7.8 (m, 13H), 6.5 (s, 1H rac), 6.45 (s, 1H, meso), 3.2 (m, 1H), 2.58 (s, 3H rac) (2.4(s, 3H, meso), 2.35 (s, 3H, meso), 1.1–1.5 (m, 21H). ESPI (88% rac): $^1$H NMR (CD$_2$Cl$_2$): δ 7.0–7.8 (m, 13H), 6.5 (s, 1H), 3.4 (m, 1H), 2.55 (s, 3H), 2.2 (s, 3H), 1.1–1.5 (m, 21H).

Example 4

Synthesis of {Me$_2$Si(4-(4-tert-Butyl-phenyl)-2-isopropyl-inden-1-yl) (2,5-dimethyl-3-(4-tert-butyl-phenyl)-cyclopento[2,3-b]thiophen-6-yl)}ZrCl$_2$.
(A-4)

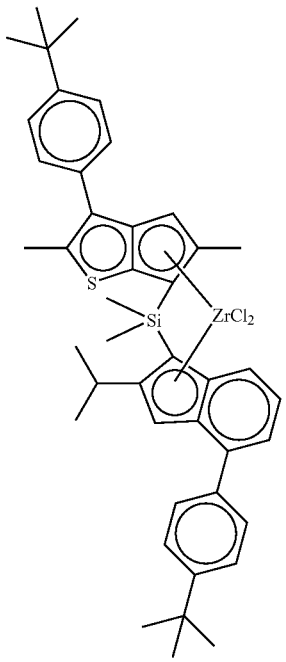

a) Synthesis of 3-Bromo-2,5-dimethyl-5,6-dihydro-cyclopenta[b]thiophen-4-one.

To a solution containing 6.64 g (40 mmol) of 2,5-dimethylcyclopenta-5,6-dihydrocyclopenta[b]thiophen-4-one, 20 g (1.1 mol) of water, and 4.1 g (50 mmol) of sodium acetate was slowly added 7.18 g (44.9 mmol) of bromine. The reaction mixture was heated to reflux, stirred for 6 h, then quenched with water. The organics were collected with dichloromethane, washed with water, dried over magnesium sulfate, filtered, then solvents were removed in vacuo. Yield: 7.82 g of bright yellow oil: 92.3% product by GC analysis: 73.7% yield. $^1$H NMR (CD$_2$Cl$_2$): δ 3.1 (m, 1H), 2.9 (m, 1H), 2.55 (s, 3H), 2.4 (m, 1H), 1.25 (d, 3H).

b) 3-(4-tert-Butyl-phenyl)-2,5-dimethyl-5,6-dihydro-cyclopenta[b]thiophen-4-one.

A mixture containing 56.9 g (231 mmol)) 3-Bromo-2,5-dimethyltcyclopenta-5,6-dihydrocyclopentathiophen-4-one, 300 ml of dimethoxyethane, 42.7 g (240 mmol) of 4-t-butylphenyl boronic acid, 19.9 g (480 mmol) of sodium carbonate and 150 ml of water was degassed and the flask atmosphere replaced with nitrogen.

To the stirred mixture was then added 0.56 g (2.3 mmol) of palladium acetate, then 0.78 g (4.6 mmol) of triphenylphosphine. The reaction mixture was then heated to reflux for 1 h, then stirred overnight. An additional 0.25 g (1 mmol) of palladium acetate and 0.35 g (2.0 mmol) of triphenylphosphine were added and the flask contents refluxed for 2 h, then poured into water. The organic phase was collected with dichloromethane, washed with water, dried over magnesium sulfate, then the solvents were removed in vacuo. 72 g of black oil were recovered which was purified by dissolving in 70% hexane/30% dichloromethane and filtering through silica. Yield: 52.2 g (75%).

c) 3-(4-tert-Butyl-phenyl)-2,5-dimethyl-6H-cyclopenta[b]thiophene.

To a solution containing 12.9 g (43 mmol) 3-(4-tert-Butyl-phenyl)-2,5-dimethyl-5,6-dihydro-cyclopenta[b]thiophen-4-one dissolved in 100 ml diethyl ether was added 22 mmol lithium aluminum hydride (1M in diethyl ether, 22 ml added) at room temperature. The reaction mixture was stirred for 2.5 h, then a saturated solution of ammonium chloride was slowly added (3 ml). The solids were filtered and the organics were collected with 30% dichloromethane/70% hexane, washed with water, dried over magnesium sulfate, filtered, then solvents removed in vacuo. The partially dehydrated product (12.3 g of a brown oil), was dissolved in 50 ml toluene and a catalytic amount of para-toluenesulfonic acid monohydride (0.25 g) was added, The flask contents were refluxed for 1 h, then stirred at room temperature overnight. The organic fraction was washed with water, dried over magnesium sulfate, filtered, then solvents removed in vacuo. Yield: 10.1 g (77.4%) dark brown oil. Olefin: (2 isomers); $^1$H NMR (CD$_2$Cl$_2$): δ 7.1–7.7 (m, 4H), 6.4–6.5 (2s, 1H), 3.18, 3.3 (2s, 2H), 2.4–2.6 (m, 3H), 2.18 (m, 3H), 1.4 (s, 12H).

d) [3-(4-tert-butyl-phenyl)-2,5-dimethyl-6H-cyclopenta[b]thiophen-6-yl]-[4-(4-tert-butyl-phenyl)-2-isopropyl-1H-inden-1-yl]-dimethyl-silane To a solution containing 5.64 g (20 mmol) 3-(4-tert-Butyl-phenyl)-2,5-dimethyl-4H-cyclopenta[b]thiophene dissolved in 50 ml of diethyl ether was added a 2.5 M solution of n-butyllithium in hexane (20 mmol, 8 ml). A catalytic amount of copper cyanide was added (0.08 g), then the reaction mixture was stirred for 3 h. The temperature was reduced to −78° C., then a solution containing 7.66 g (20 mmol) chloro-(2-isopropyl-4-(4-tert-butyl-phenyl)-1H-inden-1-yl)-dimethyl-silane dissolved in 20 ml diethyl ether was added drop-wise. After addition was complete, the flask was allowed to warm to room temperature and stirring was continued for 5 h, then poured into a saturated solution of ammonium chloride. The organic fraction was collected with a 30% dichloromethane/70% hexane solution, washed with 2N HCl, saturated bicarbonate, water, then dried over magnesium sulfate. The reaction product was filtered, then solvents removed in vacuo. Yield: 11.92 g (92%) light orange powder.

e) {Me$_2$Si(4-(4-tert-Butyl-phenyl)-2-isopropyl-inden-1-yl)(2,5-dimethyl-3-(4-tert-butyl-phenyl)-cyclopento[2,3-b]thiophen-6-yl)}ZrCl$_2$ To a solution containing 3.14 g (5 mmol) [3-(4-tert-Butyl-phenyl)-2,5-dimethyl-6H-cyclopenta[b]thiophen-6-yl]-[4-(4-tert-butyl-phenyl)-2-isopropyl-1H-inden-1-yl]dimethyl-silane dissolved in 100 ml diethyl ether was added a 2.5 M solution of n-butyllithium in hexane (10 mmol, 4 ml). The reaction mixture was stirred for 18 h, then 1.16 g (5 mmol) zirconium tetrachloride was slowly added as a dry powder. Stirring was continued for 8 h, then the mixture was filtered, then solids were washed with fresh diethyl ether. The ether insoluble solids were extracted with dichloromethane, filtered, and the solvents removed in vacuo: 0.9 g (bright yellow powder) (yield: 23%, 81% rac isomer);

$^1$H NMR (CD$_2$Cl$_2$): δ 7.3–7.7 (m, 11H), 7.1 (m, 1H), 6.5 (s, 1H rac), 3.4 (m, 1H), 2.58 (s, 3H rac), 2.2 (s, 3H), 1.1–1.5 (m, 30H).

Example 5

Synthesis of {Me$_2$Si(2-Me-5-iPr-3-(4-tert-butyl-phenyl)-cyclopento[2,3-b]thiophen-6-yl)(2-Me-4-(4-tert-butyl-phenyl)-inden-6-yl}ZrCl$_2$ (A-5)

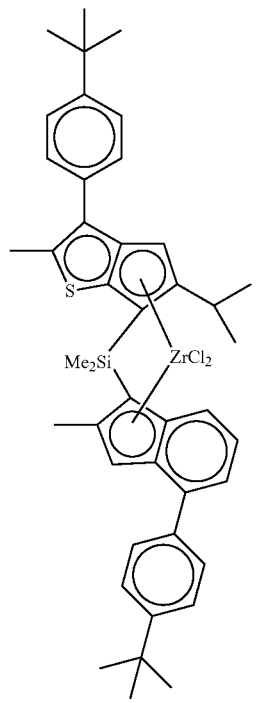

a) Synthesis of [3-(4-tert-Butyl-phenyl)-5-isopropyl-2-methyl-6H-cyclopenta[b]thiophen-6-yl]-chloro-dimethyl-silane.

3-(4-tert-Butyl-phenyl)-5-isopropyl-2-methyl-6H-cyclopenta[b]thiophene (12.59 g, 0.041 mol) was dissolved in a mixture of THF (15 mL) and toluene (50 mL). At 0° C., 18.5 mL of butyllithium in toluene (2.5 M, 0.46 mol) were added slowly. After stirring at room temperature for 3 h, the mixture was cooled to 0° C. and 15.7 g (0.121 mol) of dichlorodimethylsilane in 50 mL THF were added slowly. The reaction mixture was warmed to room temperature, stirred for 3 h, and volatiles were removed in vacuo: The residue was stirred in 75 mL of dichloromethane, filtered to remove LiCl, then volatiles were removed from the filtrate in vacuo. Yield: 16 g of crude product used without further purification. EIMS: m/z (%) 402 (M$^+$, 100), 387 (80), 360 (4), 345 (4), 309 (35), 294 (15), 279 (20), 279 (20), 264 (10), 237 (20), 221 (8), 202 (5).

b) Synthesis of [3-(4-tert-Butyl-phenyl)-5-isopropyl-2-methyl-6H-cyclopenta[b]thiophen-6-yl]-[4-(4-tert-butyl-phenyl)-2-methyl-1H-inden-1-yl]-dimethyl-silane The chlorosilane prepared above was dissolved in 25 mL of THF, cooled to −40° C., and treated with a 50/50 THF/toluene solution (60 mL) of the lithium salt of 4-(4-tert-Butyl-phenyl)-2-methyl-1H-indene at −40° C. After stirring for 7 h at room temperature, the reaction mixture was quenched by adding 15 mL of a saturated aqueous solution of NH$_4$Cl. The organic layer was separated, washed with water, dried (MgSO$_4$), and evaporated to an oil (26 g). The crude product was chromatographed on silica (10% CH$_2$Cl$_2$ in hexanes). Yield: 13 g of the dimethylsilyl bridged ligand isolated (54% yield). $^1$H-NMR δ (CDCl$_3$): (mixture of isomers) 7.1–7.5 (m, 11H), 7.3–7.5 (m, 11H), 6.5–6.9 (6 singlets, 2H total), 3.7–4.0 (4 singlets, 2H total), 2.59, 2.58, 2.50, 2.38 (4 singlets, 6H total), 1.05–1.18 (m, 7H, –0.25, –0.21, 0.1, 0.3 (4 singlets, 6H total).

b) Synthesis of {Me$_2$Si(2-Me-5-iPr-3-(4-tert-butyl-phenyl)-cyclopento[2,3-b]thiophen-6-yl)(2-Me-4-(4-tert-butyl-phenyl)-inden-6-yl}ZrCl$_2$.

6.22 g (0.010 mol) of the dimethylsilyl ligand above were dissolved in 75 mL of ether, treated with 8.2 mL of butyllithium in hexanes (2.5 M, 0.021 mol), and stirred at 40° C. for 6 h. ZrCl$_4$ (2.3 g, 0.010 mol) was added, and the mixture was stirred for 18 h. The resulting yellow precipitate was collected on a closed frit (5.5 g), and the filtrate evaporated to orange solids (3.3 g). The yellow precipitate was stirred in dichloromethane (150 mL), filtered, and solvent removed from the filtrate to give 3.8 g of zirconocene (51%, 60:40 rac:meso ratio). A 12:1 rac:meso sample (1.0 g) was obtained by slow evaporation of a dichloromethane/hexane solution of the zirconocene. $^1$H-NMR δ (CDCl$_3$): (rac isomer) 7.6–7.7 (m, 3H), 7.4–7.55 (m, 7H), 7.08 (s, 1H), 6.6 (s, 1H), 3.2 (m, 1H), 2.6 (s, 3H), 2.4 (s, 3H), 1.58 (s, 9H), 1.56 (s, 9H), 1.3 (s, 3H), 1.18 (s, 3H), 1.1 (d, 3H), 0.95 (d, 3H).

Example 6

Synthesis of {Dimethyl-silyl-(5-isopropyl-2-methyl-3-phenyl-cyclopento[2,3-b]thiophen-6-yl)-(2-methyl-4-phenyl-[3a,4-dihydro]azulen-1-yl)}ZrCl$_2$
(A-6)

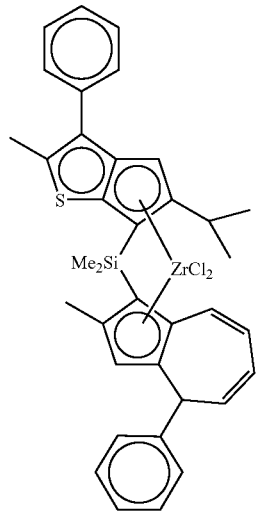

a) Synthesis of 2-methyl-4-phenyl-[3a,4-dihydro]azulenyl-lithium ether complex.

2-methyl-azulene (10 g, 0.70 mol) was dissolved in ether (100 mL), cooled to –78° C., and treated with 47 mL of phenyllithium (1.8 M sol. in cyclohexane/ether, 0.84 mol). After stirring at room temperature for 16 h, the ether was partially evaporated under reduced pressure and pentane (75 mL) was added to further precipitate the lithium salt. The lithium anion was collected on a closed frit, washed with pentane, and dried in vacuo. Yield: 18 g (86%). $^1$H-NMR δ (THF): 7.2 (d, 2H), 7.1 (t, 2H), 6.95 (t, 1H), 6.55 (d, 1H), 5.75 (m, 1H), 5.5 (m, 2H), 5.25 (m, 1H), 4.9 (s, 1H), 4.45 (d, 1H), 2.0 (s, 3H).

b) Synthesis of Chloro-dimethyl-(2-methyl-4-phenyl-3,4-dihydro-azulen-1-yl)-silane.

A portion of the lithio-ether complex above (4.9 g, 0.016 mol) was dissolved in 50 mL of THF at 0° C., cooled to –78° C., and treated with 4 mL (4.25 g, 0.033 mol) of dichlorodimethylsilane. The reaction mixture was warmed to room temperature and stirred for 24 h. THF and unreacted dichlorodimethylsilane were removed under reduced pressure. The residue was extracted with pentane (75 mL), filtered, and the filtrate evaporated to an oil. Yield: 95%. EIMS: m/z (%) 312 (M$^+$, 62), 219 (100), 203 (78), 189 (16), 165 (10), 141 (17), 115 (16), 93 (78).

c) Synthesis of (5-Isopropyl-2-methyl-3-phenyl-6H-cyclopenta[b]thiophen-6-yl)-(2-methyl-4-phenyl-3,4-dihydro-azulen-1-yl)-dimethyl-silane.

The chlorosilane above (ca. 0.016 mol) was redissolved in 50 mL of THF. The lithium salt of 5-isopropyl-2-methyl-3-phenyl-6H-cyclopenta[b]thiophene was prepared in a separate flask by reacting 0.016 mol of 5-isopropyl-2-methyl-3-phenyl-6H-cyclopenta[b]thiophene dissolved in ether (60 mL) with butyllithium (6.7 mL of 2.5 M solution in hexanes, 0.17 mmol) for 4 h, addition of 0.13 mL of N-methyimidazole, stirring for 15 min., and addition of 10 mL of THF at 0° C. to completely dissolve the lithium salt. The anion solution was then added slowly to the chlorosilane solution at –78° C. After stirring overnight at room temperature, water (30 mL) was added slowly, the organic layer was separated, dried (MgSO$_4$), and evaporated to an oil. The oil was chromatographed on silica (5% MeCl$_2$ in hexane) giving 6 g of dimethylsilyl bridged ligand as a white solid. Yield; 70%. EIMS: m/z (%) 530 (M$^+$, 1), 331 (2), 310 (20), 275 (30), 253 (10), 207 (100), 191 (10), 163 (2), 133 (6), 96 (9).

c) Synthesis of Dilithio-ether Complex of (5-Isopropyl-2-methyl-3-phenyl-6H-cyclopenta[b]thiophen-6-yl)-dimethyl-(2-methyl-4-phenyl-3,4-dihydro-azulen-1-yl)-silane.

The dimethyl silyl bridged ligand prepared above (5.7 g, 0.011 mol) was dissolved in 60 mL of ether, cooled to –78° C., and treated with 9 mL of butyllithium (2.5 M sol. in hexanes, 0.023 mol). After stirring overnight at room temperature, solvents were removed under reduced pressure and the solid residue was stirred in 60 mL of hexane. The tan colored solids were collected on a closed frit, washed with pentane, and dried in vacuo (yield 5.76 g, 82%). $^1$H-NMR δ (THF): 7.0–7.6 (m, 10H), 5.9 (s, 1H), 5.8 (m, 1H), 5.4–5.5 (m, 3H), 5.0 (s, 1H), 4.3 (d, 1H), 3.2 (m, 1H), 2.45 (s, 3H), 2.13 (s, 3H), 1.2 (t, 3H), 0.9 (t, 3H), 0.6 (2 singlets, 6H).

d) Synthesis of {Dimethyl-silyl-(5-isopropyl-2-methyl-3-phenyl-cyclopento[2,3-b]thiophen-6-yl)-(2-methyl-4-phenyl-[3a,4-dihydro]azulen-1-yl)}ZrCl$_2$ A 250 mL round bottom flask was charged with the dilithio salt prepared above (5.7 g, 0.009 mol) and ZrCl$_4$ (2.17 g, 0.009 mol). After cooling to –78° C., hexane (50 mL) and ether (50 mL) were added and the mixture stirred for 16 h at room temperature. The resulting yellow precipitate (3.5 g) was collected on a closed frit, extracted with dichloromethane (100 mL), and filtered through a pad of celite giving 1.95 g of the zirconocene after evaporation of solvent (ca 8:1 rac:meso ratio). Yield: 31%. $^1$H-NMR δ (CDCl$_3$): (rac isomer) 7.2–7.6 (m, 9H), 7.0 (d, 1H), 6.6 (s, 1H), 6.2 (m, 1H), 5.8–6.0 (m, 3H), 5.65 (s, 1H), 4.95 (broad s, 1H), 3.1 (m, 1H), 2.6 (s, 3H), 2.2 (s, 3H), 1.3 (d, 3H), 1.14 (d, 3H), 1.0 (2 singlets, 6H).

Examples 5–10 and Comparative Example 11

Propylene/Ethylene Polymerization

Polymerization grade propylene was further purified by passing through columns of 3A molecular sieves and alumina. A 10 wt % solution of methylalumoxane (MAO) in toluene was purchased from Witco Corp. and used as received. Polymerizations were conducted in a 4 L stainless steel autoclave equipped with an air-driven Magnadrive (Autoclave Engineers Co.) stirrer and steam/water temperature controlled jacket. The autoclave was swept with dry argon at 90° C. for 1 h prior to polymerization. An amount of the metallocene compounds indicated in Table 1 was dissolved in 5 ml of a 10 wt % toluene solution of MAO, shaken for 10 minutes, and added to the reactor at 15° C. 2.2 L of propylene were added to the reactor, the stirrer was set at 300 rpm, the reactor was thermostated at 45° C., and ethylene overpressure was added. The zirconocene/MAO solution was then charged to the reactor through a stainless steel tube using a controlled amount of argon gas pressure. The reactor and contents were heated to 70° C. in ca. 5 minutes while ethylene was fed on demand with a mass flow controller to maintain the desired reactor overpressure. Constant overpressure was maintained throughout the run. In all polymerization tests, carbon monoxide gas was charged to the reactor 1 h after reaching polymerization temperature and the residual monomer was vented while cooling the reactor to room temperature. The polymer was removed and dried in a vacuum oven at 50° C. for 1 h before weighing. Reported activities were calculated from polymer and zirconocene weights. Solution intrinsic viscosity $[\eta]_o$ of polymer samples were determined in Decalin at 135° C. Transition temperature and enthalpy of melting and crystallization of homopolymer samples were measured using a power-compensation mode Perkin Elmer (PE) DSC-7 and PE PYRIS (revision 3.03) software. A PE Intercooler II (Model FC100PEA) was used for cooling. The instrument was calibrated against certified (1) indium with Teim=156.60° C.; $H_f$=28.71 J/g and (2) tin with Teim 231.88° C.; Hf=60.46 J/g. The dynamic heating/cooling rate was 20° C./min. The purge gas was nitrogen flowing at 20±2 cc/min. A three ramp (heat-cool-reheat) procedure was employed with upper and lower temperature limits of 25° C. and 235° C., respectively. The isothermal hold time between ramps was 3 min. The results of the second heat are reported. Weight percent ethylene of E/P copolymer samples was determined by IR spectroscopy of pressed film polymer samples. Polymerization results are collected in Table 1.

TABLE 1

| EX | Zirconocene (mg) | Pol. T, ° C. | Yield, g | Activity, Kg/g-met.h | Wt % $C_2H_4$ | $[\eta]_o$; dL/g |
|---|---|---|---|---|---|---|
| 5 | A-1 (0.05) | 70 | 50 | 1,000 | 4.3 | 2.1 |
| 6 | A-1 (0.05) | 70 | 133 | 5,320 | 12.8 | 2.8 |
| 7 | A-2 (0.1) | 70 | 300 | 4,000 | 5.2 | 2.8 |
| 8 | A-2 (0.05) | 70 | 198 | 7,920 | 9.8 | 3.3 |
| 9 | A-3 (0.1) | 70 | 48 | 640 | 6.4 | 2.3 |
| 10 | A-4 (0.1) | 70 | 56 | 747 | 10.7 | 3.1 |
| 11* | C-1 (0.05) | 50 | 235 | 4,700 | 9.9 | 1.4 |

*comparative

Examples 12–14

Catalyst formation. 0.206 mmol of metallocene dichloride indicated in Table 2 have been added at room temperature to 4.33 mmol of MAO (30 wt. % solution in toluene supplied by Albemarle). The concentrated solution has been stored over night at room temperature (r.t.) and has been diluted afterwards with 10.9 ml of toluene. The solution has been carefully added to 10 g of silica (Sylopol 948 calcinated at 600° C. supplied by Grace). Special attention has been paid to a uniform distribution of the coloured solution over the supporting material. After 10 min the flask with the catalyst mud has been transferred to a vacuum line, on which it has been dried until the content of residual volatiles has been reduced under 5 wt. %.

Polymerizations.

Copolymer blends have been generated in a 24 l reactor. Before filling the reactor has been inertized with nitrogen. 10 l of liquid propylene and 8 ml of a solution of 20 wt. % triethylaluminium in Exsol (Crompton) have been added to the reactor and the mixture has been stirred at 30° C. for 15 min. The polymerizations themselves have been performed following a two-step procedure: A homopolymerization step without hydrogen for 30 min is followed by a copolymerization step for another 30 min. The homopolymerization step has been performed by adding a suspension of the respective catalyst in 20 ml exsol to the reactor. The reactor temperature has been lifted to 65° C. and kept at this temperature for 30 min. Afterwards 10 bar of ethylene have been added and the pressure and the reactor temperature have been kept constant for another 30 min. Finally the reactor has been vented and the yielded polymer blend has been dried under vacuum.

Fractionation of the copolymer blends: The polymer blends out of the copolymerizations have been fractionated as follows: 5 g of the polymer blend has been suspended in 1 l of Exsol 140/170 (stabilized with 0.1% of Irganox 1010 and purged with nitrogen before use) and has been dissolved slowly stirred under nitrogen by heating up to 130° C. With a stirring speed of 350 rpm the solution is cooled to 50° C. and kept for 15 min at this temperature. The crystallized polymer has been isolated on a filter, the supernatant solvent removed and the solid has been washed with small amounts of Exsol. The dissolving/crystallizing-procedure has been repeated a second time. The so called "crystalline fraction" has been isolated on a frit D3 and dried under vacuum. The Exsol-solutions deriving from the filtration and washing steps have been combined and condensed to a volume of about 250 ml. The dissolved polymer has been precipitated with 1 l of acetone and isolated on a frit D1. The wet polymer has been extracted for 4 h under reflux with 280 ml diethyl ether (stabilized with 0.1% Irganox 1010). The so called "(amorphous) etherinsoluble fraction" has been isolated on a frit D3 and dried under vacuum. The ether solution has been condensed to 50 ml. The dissolved polymer has been precipitated with a surplus of acetone and isolated on a frit D1. This so called "(amorphous) ethersoluble fraction" has been isolated under vacuum. The polymerization are reported in Table 2; characterization of polymers fractions is reported in Table 3

TABLE 2

| Ex | Zirconocene | Catalyst (mg) | Activity, Kg/g * h |
|---|---|---|---|
| 12 | A-1 | 1500 | >3 |
| 13 | A-2 | 1000 | 0.97 |
| 14 | A-5 | 1500 | 0.45 |

TABLE 3

| | crystalline fraction | | Ether insoluble fraction | | | ether soluble fraction | |
|---|---|---|---|---|---|---|---|
| Ex | % | I.V. | % | I.V. | C2 % w | % | I.V. |
| 12 | 18.8 | 2.42 | 60.8 | 2.28 | 8.0 | 20.4 | 2.19 |
| 13 | 16.9 | 2.91 | 77.8 | 3.13 | 10.5 | 5.2 | 1.83 |
| 14 | 36.4 | 2.66 | 53.6 | 3.46 | 10.6 | 9.7 | 2.66 |

% = fraction of the polymer with respect to the total polymer fractionated

The invention claimed is:
1. A metallocene compound of formula (I):

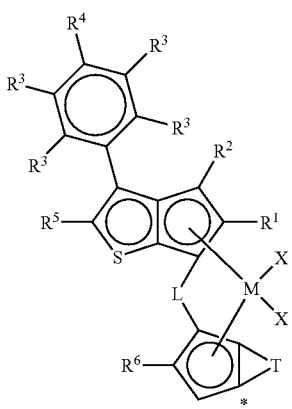

(I)

wherein

M is zirconium, hafnium or titanium;

X, equal to or different from each other, is a hydrogen atom, a halogen atom, a R, OR, OR'O, $OSO_2CF_3$, OCOR, SR, $NR_2$ or $PR_2$ group, wherein R is a linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl, or $C_7$–$C_{20}$-arylalkyl radical, optionally containing one or more heteroatoms belonging to groups 13–17 of the Periodic Table of the Elements; and the R' substituent is a divalent group selected from $C_1$–$C_{40}$-alkylidene, $C_6$–$C_{40}$-arylidene, $C_7$–$C_{40}$-alkylarylidene or $C_7$–$C_{40}$-arylalkylidene radicals; two X can also join to form a $C_4$–$C_{40}$ dienyl ligand;

$R^1$ is a linear or branched, saturated or unsaturated $C_1$–$C_{40}$-alkyl, $C_3$–$C_{40}$-cycloalkyl, $C_6$–$C_{40}$-aryl, $C_7$–$C_{40}$-alkylaryl, or $C_7$–$C_{40}$-arylalkyl radical, optionally containing one or more heteroatoms belonging to groups 13–17 of the Periodic Table of the Elements;

$R^2$, $R^3$, $R^4$ and $R^5$, equal to or different from each other, are hydrogen atoms, halogen atoms, or linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl, or $C_7$–$C_{20}$-arylalkyl radicals, optionally containing one or more heteroatoms belonging to groups 13–17 of the Periodic Table of the Elements;

$R^6$ is a linear or branched, saturated or unsaturated $C_1$–$C_{40}$-alkyl, $C_3$–$C_{40}$-cycloalkyl, $C_6$–$C_{40}$-aryl, $C_7$–$C_{40}$-alkylaryl, or $C_7$–$C_{40}$-arylalkyl radical, optionally containing one or more heteroatoms belonging to groups 13–17 of the Periodic Table of the Elements;

L is a divalent bridging group selected from $C_1$–$C_{20}$ alkylidene, $C_3$–$C_{20}$ cycloalkylidene, $C_6$–$C_{20}$ arylidene, $C_7$–$C_{20}$ alkylarylidene, or $C_7$–$C_{20}$ arylalkylidene optionally containing heteroatoms belonging to groups 13–17 of the Periodic Table of the Elements, or a silylidene radical containing up to 5 silicon atoms;

T is a radical of formula (II), (III), (IV) or (V):

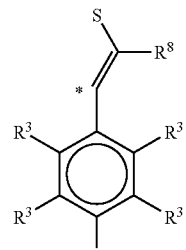

(II)

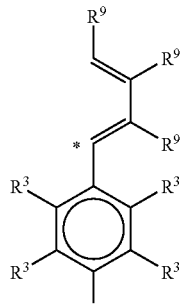

(III)

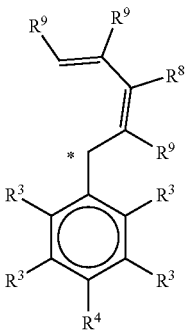

(IV)

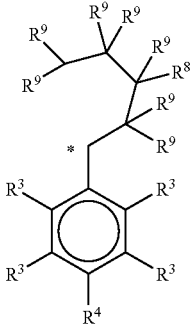

(V)

wherein the atom marked with the symbol * bonds the atom marked with the same symbol in the compound of formula (I);

$R^8$ is a hydrogen atom or a linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl, or $C_7$–$C_{20}$-arylalkyl radical, optionally containing one or more heteroatoms belonging to groups 13–17 of the Periodic Table of the Elements;

$R^9$, equal to or different from each other, is a hydrogen atom or a linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl, or $C_7$–$C_{20}$-arylalkyl radical, optionally containing one or more heteroatoms belonging to groups 13–17 of the Periodic Table of the Elements;

with the proviso that at least one group between $R^1$ and $R^6$ is a group of formula $C(R^{11})_2R^{12}$ wherein $R^{11}$, equal to or different from each other, is a linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl, or $C_7$–$C_{20}$-arylalkyl radical, optionally containing one or more heteroatoms belonging to groups 13–17 of the Periodic Table of the Elements; or two $R^{11}$ groups can join to form a $C_3$–$C_{20}$ saturated or unsaturated ring; and $R^{12}$ is a hydrogen atom, a linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl, or $C_7$–$C_{20}$-arylalkyl radical, optionally containing one or more heteroatoms belonging to groups 13–17 of the Periodic Table of the Elements.

2. The metallocene compound according to claim 1 wherein at least one $R^4$ is a group —$C(R^7)_3$, wherein $R^7$, equal to or different from each other, is a linear or branched, saturated or unsaturated $C_1$–$C_{20}$-alkyl radical.

3. The metallocene compound according to claim 1 wherein X is a halogen atom, a R, OR'O or OR group wherein R is a linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl, or $C_7$–$C_{20}$-arylalkyl radicals, optionally containing one or more heteroatoms belonging to groups 13–17 of the Periodic Table of the Elements; and the R' substituent is a divalent group selected from $C_1$–$C_{20}$-alkylidene, $C_6$–$C_{20}$-arylidene, $C_7$–$C_{20}$-alkylarylidene, or $C_7$–$C_{20}$-arylalkylidene radicals.

4. The metallocene compound according to claim 1 wherein L is $Si(CH_3)_2$, $SiPh_2$, $CH_2$, $(CH_2)_2$, $(CH_2)_3$ or $C(CH_3)_2$.

5. The metallocene compound according to claim 1 wherein $R^1$, $R^5$, $R^6$ and $R^8$, equal to or different from each other, are linear or branched, saturated or unsaturated $C_1$–$C_{20}$-alkyl radicals.

6. A process for the preparation of propylene copolymers having a propylene derived units content of at least 50% by weight, comprising the step of contacting, under polymerization conditions, propylene with one or more alpha olefins of formula $CH_2$=CHA, wherein A is hydrogen or a $C_2$–$C_{20}$ alkyl radical, in the presence of a catalyst system obtained by contacting:

a) a metallocene compound of formula (I):

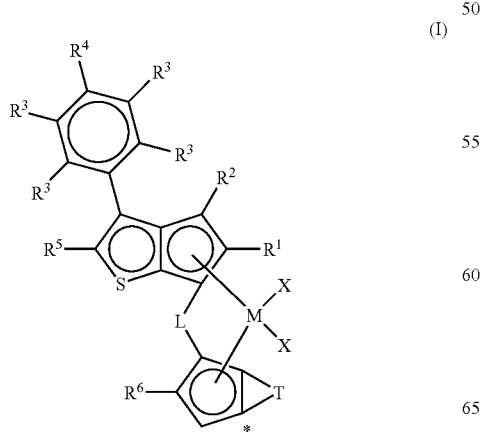

(I)

wherein

M is zirconium, hafnium or titanium;

X, equal to or different from each other, is a hydrogen atom, a halogen atom, a R, OR, OR'O, $OSO_2CF_3$, OCOR, SR, $NR_2$ or $PR_2$ group, wherein R is a linear or branched, saturated or unsaturated $C_1$–$C_{20}$-alkyl, $C_3$–$C_{20}$-cycloalkyl, $C_6$–$C_{20}$-alkylaryl, or $C_7$–$C_{20}$-arylalkyl radical, optionally containing one or more heteroatoms belonging to groups 13–17 of the Periodic Table of the Elements: and the R' substituent is a divalent group selected from $C_1$–$C_{40}$-alkylidene, $C_6$–$C_{40}$-arylidene, $C_7$–$C_{40}$-alkylarylidene or $C_7$–$C_{40}$-arylalkylidene radicals; two X can also join to form a $C_4$–$C_{40}$ dienyl ligand;

$R^1$ is a linear or branched, saturated or unsaturated $C_1$–$C_{40}$-alkyl, $C_3$–$C_{40}$-cycloalkyl, $C_6$–$C_{40}$-aryl, $C_7$–$C_{40}$-alkylaryl, or $C_7$–$C_{40}$-arylalkyl radical, optionally containing one or more heteroatoms belonging to groups 13–17 of the Periodic Table of the Elements;

$R^2$, $R^3$, $R^4$ and $R^5$, equal to or different from each other, are hydrogen atoms, halogen atoms, or linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl, or $C_7$–$C_{20}$-arylalkyl radicals, optionally containing one or more heteroatoms belonging to groups 13–17 of the Periodic Table of the Elements;

$R^6$ is a linear or branched, saturated or unsaturated $C_1$–$C_{40}$-alkyl, $C_3$–$C_{40}$-cycloalkyl, $C_6$–$C_{40}$-aryl, $C_7$–$C_{40}$-alkylaryl, or $C_7$–$C_{40}$-arylalkyl radical, optionally containing one or more heteroatoms belonging to groups 13–17 of the Periodic Table of the Elements;

L is a divalent bridging group selected from $C_1$–$C_{20}$ alkylidene, $C_3$–$C_{20}$ cycloalkylidene, $C_6$–$C_{20}$ arylidene, $C_7$–$C_{20}$ alkylarylidene, or $C_7$–$C_{20}$ arylalkylidene optionally containing heteroatoms belonging to groups 13–17 of the Periodic Table of the Elements, or a silylidene radical containing up to 5 silicon atoms, T is a radical of formula (II), (III), (IV) or (V):

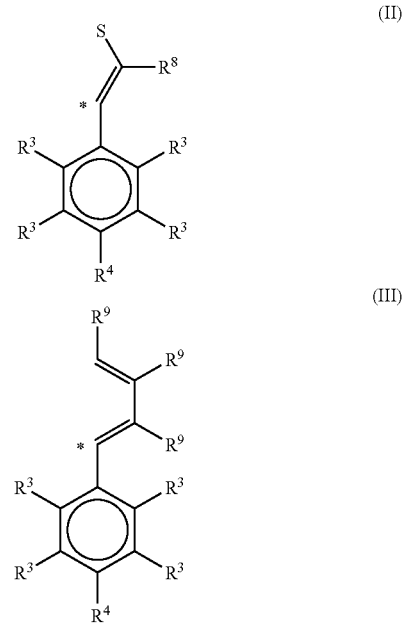

-continued

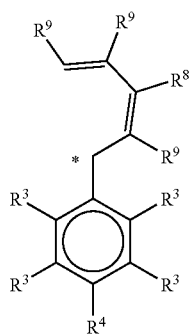
(IV)

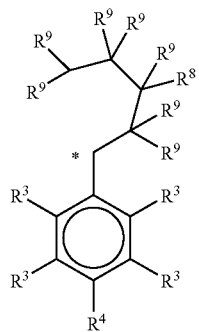
(V)

wherein
the atom marked with the symbol * bonds the atom marked with the same symbol in the compound of formula (I);

$R^8$ is a hydrogen atom or a linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl, or $C_7$–$C_{20}$-arylalkyl radical, optionally containing one or more heteroatoms belonging to groups 13–17 of the Periodic Table of the Elements, $R^9$, equal to or different from each other, is a hydrogen atom or a linear or branched, saturated or unsaturated $C_1$–$C_{20}$-alkyl, $C_3$–$C_{20}$-cycloalkyl, $C_6$–$C_{20}$-alkylaryl, or $C_7$–$C_{20}$-arylalkyl radical, optionally containing one or more heteroatoms belonging to groups 13–17 of the Periodic Table of the Elements;

with the proviso that at least one group between $R^1$ and $R^6$ is a group of formula $C(R^{11})_2R^{12}$ wherein $R^{11}$, equal to or different from each other, is a linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl, or $C_7$–$C_{20}$-arylalkyl radical, optionally containing one or more heteroatoms belonging to groups 13–17 of the Periodic Table of the Elements; or two $R^{11}$ groups can join to form a $C_3$–$C_{20}$ saturated or unsaturated ring; and $R^{12}$ is a hydrogen atom, a linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl, or $C_7$–$C_{20}$-arylalkyl radical, optionally containing one or more heteroatoms belonging to groups 13–17 of the Periodic Table of the Elements, and b) an alumoxane or a compound that forms an alkylmetallocene cation.

7. The process according to claim 6 wherein the catalyst system is obtained by further contacting an organo aluminum compound.

8. The process according to claim 6 wherein the catalysts system is supported on an inert carrier.

9. A process for preparing the compound of formula (I)

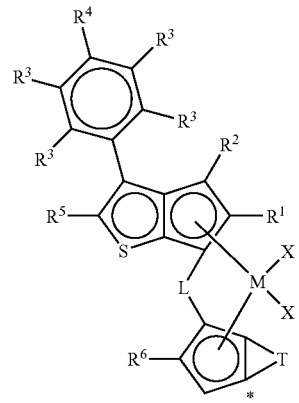
(I)

wherein
M is zirconium, hafnium or titanium;

X, equal to or different from each other, is a hydrogen atom, a halogen atom, a R, OR, OR'O, $OSO_2CF_3$, OCOR, SR, $NR_2$ or $PR_2$ group, wherein R is a linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl, or $C_7$–$C_{20}$-arylalkyl radical, optionally containing one or more heteroatoms belonging to groups 13–17 of the Periodic Table of the Elements; and the R' substituent is a divalent group selected from $C_1$–$C_{40}$-alkylidene, $C_6$–$C_{40}$-arylidene, $C_7$–$C_{40}$-alkylarylidene or $C_7$–$C_{40}$-arylalkylidene radicals; two X can also join to form a $C_4$–$C_{40}$ dienyl ligand;

$R^1$ is a linear or branched, saturated or unsaturated $C_1$–$C_{40}$-alkyl, $C_3$–$C_{40}$-cycloalkyl, $C_6$–$C_{40}$-aryl, $C_7$–$C_{40}$-alkylaryl, or $C_7$–$C_{40}$-arylalkyl radical, optionally containing one or more heteroatoms belonging to groups 13–17 of the Periodic Table of the Elements;

$R^2$, $R^3$, $R^4$ and $R^5$, equal to or different from each other, are hydrogen atoms, halogen atoms, or linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl, or $C_7$–$C_{20}$-arylalkyl radicals, optionally containing one or more heteroatoms belonging to groups 13–17 of the Periodic Table of the Elements;

$R^6$ is a linear or branched, saturated or unsaturated $C_1$–$C_{40}$-alkyl, $C_3$–$C_{40}$-cycloalkyl, $C_6$–$C_{40}$-aryl, $C_7$–$C_{40}$-alkylaryl, or $C_7$–$C_{40}$-arylalkyl radical, optionally containing one or more heteroatoms belonging to groups 13–17 of the Periodic Table of the Elements;

L is a divalent bridging group selected from $C_1$–$C_{20}$ alkylidene, $C_3$–$C_{20}$ cycloalkylidene, $C_6$–$C_{20}$ arylidene, $C_7$–$C_{20}$ alkylarylidene, or $C_7$–$C_{20}$ arylalkylidene optionally containing heteroatoms belonging to groups 13–17 of the Periodic Table of the Elements, or a silylidene radical containing up to 5 silicon atoms:

T is a radical of formula (II), (III), (IV) or (V):

(II)
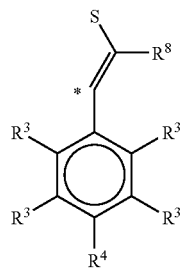

(III)
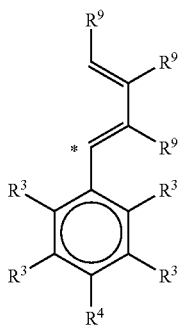

(IV)
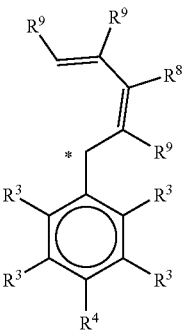

(V)
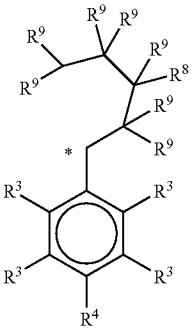

wherein
the atom marked with the symbol * bonds the atom marked with the same symbol in the compound of formula (I);

$R^8$ is a hydrogen atom or a linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl, or $C_7$–$C_{20}$-arylalkyl radical, optionally containing one or more heteroatoms belonging to groups 13–17 of the Periodic Table of the Elements;

$R^9$, equal to or different from each other, is a hydrogen atom or a linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl, or $C_7$–$C_{20}$-arylalkyl radical, optionally containing one or more heteroatoms belonging to groups 13–17 of the Periodic Table of the Elements;

with the proviso that at least one group between $R^1$ and $R^6$ is a group of formula $C(R^{11})_2R^{12}$ wherein $R^{11}$, equal to or different from each other, is a linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl, or $C_7$–$C_{20}$-arylalkyl radical, optionally containing one or more heteroatoms belonging to groups 13–17 of the Periodic Table of the Elements; or two $R^{11}$ groups can join to form a $C_3$–$C_{20}$ saturated or unsaturated ring; and $R^{12}$ is a hydrogen atom a linear or branched, saturated or unsaturated $C_1$–$C_{20}$-alkyl, $C_3$–$C_{20}$-cycloalkyl, $C_6$–$C_{20}$-aryl, $C_7$–$C_{20}$-alkylaryl, or $C_7$–$C_{20}$-arylalkyl radical, optionally containing one or more heteroatoms belonging to groups 13–17 of the Periodic Table of the Elements the process comprising the step of contacting a ligand of formula (Ia)

(Ia)
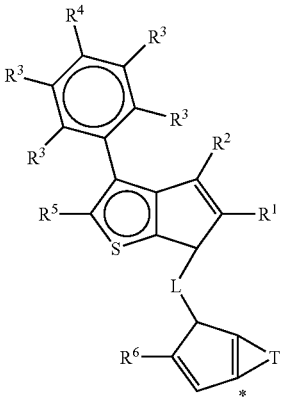

or one of its double bonds isomers with at least two equivalents of a base, selected from the group consisting of metallic sodium and potassium, sodium and potassium hydroxide and an organolithium compound, and then contacting the obtained salt with a compound of formula $MX_4$.

10. The process of claim 9 wherein the base is butyllithium.

* * * * *